United States Patent [19]
Dukes et al.

[11] Patent Number: 5,205,296
[45] Date of Patent: * Apr. 27, 1993

[54] UTERINE CONTRACTION DETECTION

[75] Inventors: John N. Dukes, Los Altos Hills; Alan P. Greenstein, Menlo Park, both of Calif.

[73] Assignee: Hewlett-Packard Company, Palo Alto, Calif.

[*] Notice: The portion of the term of this patent subsequent to Dec. 8, 2009 has been disclaimed.

[21] Appl. No.: 885,579

[22] Filed: May 19, 1992

Related U.S. Application Data

[63] Continuation of Ser. No. 607,217, Oct. 30, 1990.

[51] Int. Cl.$^5$ .............................................. A61B 5/11
[52] U.S. Cl. ...................................... 128/775; 73/574; 73/576
[58] Field of Search ................... 128/775; 73/574, 576

[56] References Cited
U.S. PATENT DOCUMENTS 2,800,647 7/1957 Baerwald et al. ...................... 73/574
3,240,054 3/1966 Roth ...................................... 73/574
4,072,046 2/1978 Lao ....................................... 73/574

Primary Examiner—Lee S. Cohen
Assistant Examiner—Robert L. Nasser, Jr.

[57] ABSTRACT

A system for tracing uterine contraction is disclosed. The system comprises a probe and an electronics module. The electronics module includes a drive circuit and an output section having a frequency counter. The output section also includes a strip-chart recorder driven by a frequency-to-voltage converter. The probe includes an electro-mechanical transducer which is driven at resonance by the action of the drive circuit. When the probe contacts the abdomen of a pregnant subject, changes in the mechanical impedance of bodily tissue during a contraction affect the resonant frequency of the probe and thus the frequency output by the drive circuit. This frequency can be read directly from the frequency counter and recorded on the strip-chart so that contractions can be traced.

7 Claims, 5 Drawing Sheets 5,205,296

UTERINE CONTRACTION DETECTION

CROSS REFERENCED TO RELATED APPLICATION

This is a continuation of application Ser. No. 07/607,217, filed on Oct. 30, 1990 pending.

BACKGROUND OF THE INVENTION

The present invention relates to a system for detecting changes in mechanical impedance and, more particularly, for tracing uterine contractions.

Uterine contraction, although a gross mechanical phenomenon, has proved awkward to measure. Typically, uterine contractions are traced by measuring the spring resistance to a toco-transducer probe which pushes against the maternal abdomen, as disclosed in Hewlett-Packard, "Cardiotocograph", Application Note 700 F., 1979. The probe is typically held in place and against the maternal abdomen by an elastic belt. When contractions occur, the probe encounters a more resistive medium and it moves orthogonal to the abdominal surface. This method generally suffices to trace uterine contraction. However, it is awkward to position the elastic belt and probe properly. Furthermore, the pressure of the elastic belt and probe are a source of discomfort to the subject.

Another widely employed method of tracing contractions is even more intrusive. Intrauterine measurement of contractions can be performed using a balloon-tipped or open-ended fluid filled catheter, as disclosed by D. O. Thorne, I. Assadi, J. Flores, and J. Seitchik, "The relationship of the maximum amplitude and the maximum and minimum slope of the intrauterine pressure waveform in late pregnancy and labor", *IEEE Transactions on Biomedical Engineering.*, vol. BME-19, p. 388, 1972.

More recently, changes in the electrical activity of tissue during contractions have been employed in tracing contractions, as disclosed by C. Marque, J. M. G. Duchene, S. Leclercq, G. S. Panczer, and J. Chaumont, in "Uterine EHG Processing for Obstetrical Monitoring", *IEEE Transactions on Biomedical Engineering*, Vol. BME-33, No. 12, December 1986. The electrical activity is recorded as a electromyogram, also referred to as a "electrohysterogram" or "EHG".

EHG measurements can be made using intrauterine or abdominal electrodes. Electrical signals at several frequencies have been observed to correlate with contractions. The main problems with EHG measurements are that the signals are not strong, so that they are easily interfered with by electrical signals from spurious physiological activity, and that their correlation with contractions is not very strong. Furthermore, intrauterine electrodes are more intrusive than desired. Abdominal electrodes are less intrusive, but pick up electrical activity resulting from other sources, such as skin stretching, respiratory movements, and movement of abdominal muscles. Because of the weakness of the electrical signals being monitored and the susceptibility of the signals to noise from sources other than the contractions of interest, the sensitivity and validity of abdominal EHG measurements are limited.

What is needed is an improved system and method for tracing uterine contractions which provides accurate tracing and which is also non-intrusive, comfortable and easy to use.

SUMMARY OF THE INVENTION

In accordance with the present invention, changes in mechanical impedance are traced by monitoring their effect on the resonant frequency of a mechanically oscillating system. Since intrauterine contractions are inevitably accompanied by changes in the mechanical impedance of abdominal tissue, they can be traced using this system and method.

The mechanically oscillating system comprises a probe, or other transducer assembly, including a mechanical interface and an electro-mechanical resonant transducer. The resonant transducer has a resonant frequency at which it vibrates preferentially; this resonant frequency varies with the mechanical impedance of a mechanically interfaced body. The mechanical interface can be simply a surface which can be adhered or otherwise positioned against an abdomen or other body of interest. This surface can be part of a probe housing which encloses the electro-mechanical transducer.

The electro-mechanical transducer can be implemented by taking advantage of a variety of phenomena, including the piezo-electric effect and electro-magnetic effects. In the latter case, the transducer can include a permanent magnet, an electro-magnet, and a spring for regulating their relative positions. An electric signal applied to the electro-magnet causes relative displacement of the magnets. By rigidly attaching one of the magnets to the mechanical interface, the latter can be made to displace adjacent tissue.

The transducer has a resonant frequency which is a function of the mechanical impedance of the spring and effective masses and mechanical impedances associated with each magnet. When the mechanical interface is adhered to an abdomen, the resonant frequency varies sensitively with the "spring constant" of the abdominal tissue. Preferably, the transducer is designed so that the range of resonant frequencies is spanned by the "low sonic" frequencies, i.e., 20 Hz to 200 Hz.

Resonant frequency is monitored using a feedback circuit which drives the transducer at its resonant frequency. The output of the feedback circuit is then a signal at the current resonant frequency of the transducer. By tracking the frequency of this output, changes in resonant frequency, and thus changes in the mechanical impedance of an abdomen, and thus, contractions can be monitored. The frequency of the feedback circuit output can be monitored using a frequency counter and display and/or using a frequency-to-voltage converter to drive a standard strip-chart recorder.

A major advantage of the present invention is that it employs an active measurement system. Instead of relying on the subject to provide the energy, whether mechanical or electrical, for the measurement system, the present invention supplies a signal which is merely modulated by the subject. In the preferred embodiment, the parameter being monitored is frequency. Frequency is easily measured with precision and is less vulnerable to interference than alternative parameters. In contrast, EHG systems depend on the passive detection of a weak electrical signal which is subject to interference by other electrical signals. Also, since contractions inevitably are accompanied by significant changes in mechanical impedance, there is no doubt as to the validity of the parameter being measured. Conveniently, the present invention disposes of the elastic belt required of typical abdominal toco-transducers. Consequently, measurement is less effected by shifting of such a belt when the subject shifts body position.

Thus, the present invention provides a system and method for tracing uterine contractions which is convenient, accurate and reliable. Furthermore, it is readily apparent that the present invention is applicable to the measurement of changes in mechanical impedance associated with other tissue changes and to a wide variety of other subjects, not necessarily living, in which changes in mechanical impedance are of interest. These and other features and advantages of the present invention are apparent from the description below with reference to the following drawing.

Figure 1:
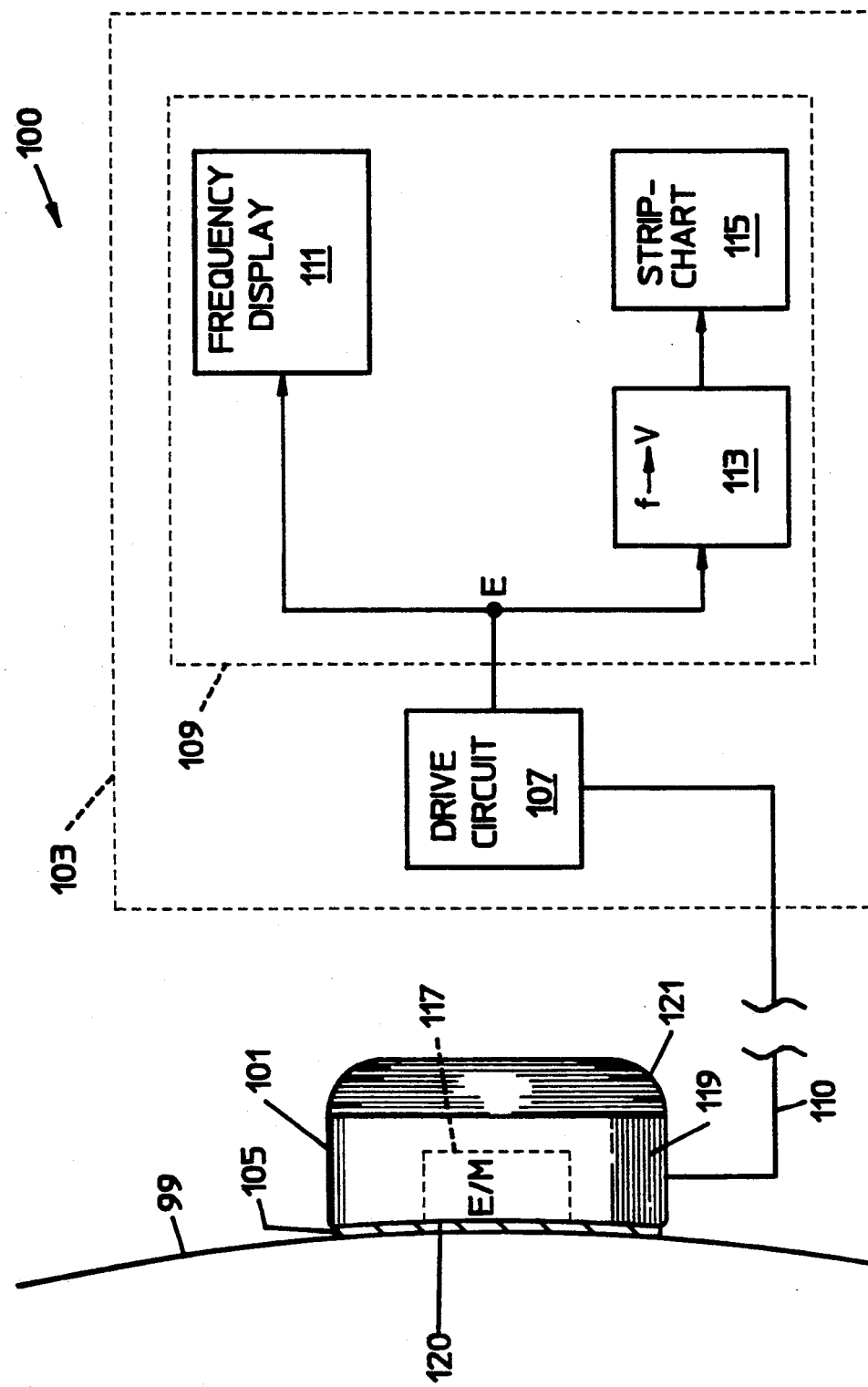
FIG. 1 is a schematic view of a system for tracing uterine contractions in accordance with the present invention.

In the figures, for elements referred to by a three-digit reference numeral, the first digit of the reference numeral is the figure number in which that element is first depicted.

DESCRIPTION OF THE PREFERRED EMBODIMENTS

In accordance with the present invention, a uterine contraction tracing system 100 comprises a probe 101 and an electronics module 103. Probe 101, can be attached to a body 99 with medical-grade, double-sided adhesive tape 105. Electronics module 103 includes a drive circuit 107 and an output section 109. Probe 101 and drive circuit 107 are electrically coupled by a cable 110 and constitute an oscillator. Output section 109 includes a frequency display 111 and a frequency-to-voltage converter 113 for driving a strip chart recorder 115.

Probe 101 incorporates a electro-mechanical ("E/M") resonant transducer 117, i.e., a transducer which has a resonant frequency enclosed by a housing 119 and a cap 121. A surface 120 of housing 119 serves, along with tape 105, as a mechanical interface with body 99. When driven by a cyclical drive signal, transducer 117 can cause probe 101 to vibrate. While not attached to a substantial object, probe 101 can be made to vibrate at a free-space resonant frequency by drive circuit 107. While attached to a substantial object, probe 101 is driven at a different resonant frequency. The instantaneous value of this frequency is a function of the mechanical impedance of body 99. Thus, by monitoring this resonant frequency, the mechanical impedance of body 99 can be traced. Since, contractions are accompanied by changes in mechanical impedance, they can be detected and characterized using uterine contraction tracing system 100.

Figure 2B:
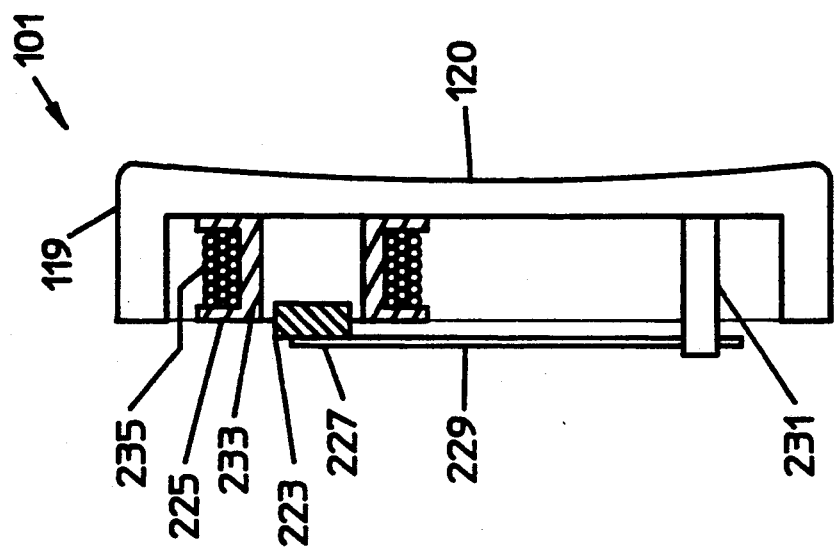
FIGS. 2A and 2B are plan and sectional views, respectively, of a probe of the system of FIG. 1 with its cover removed.
Figure 2A:
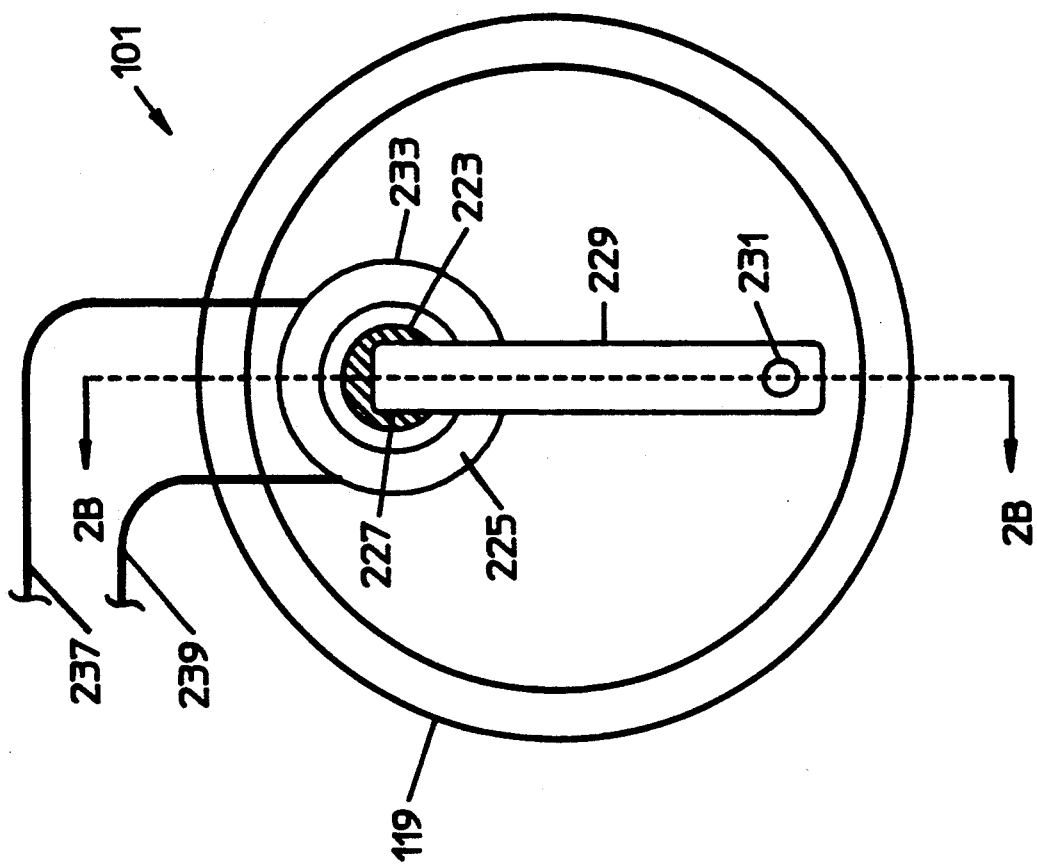

Transducer 117 comprises a permanent magnet 223 and an electro-magnet 225, shown in FIGS. 2A and 2B. Permanent magnet 223 is bonded at the free end 227 of a leaf spring 229 cantilevered from a support post 231 rigidly attached to housing 119. Electro-magnet 225 comprises a plastic bobbin 233 and a conductive coil 235 which surrounds permanent magnet 223 as shown in FIG. 2B. Coil 235 has a signal lead 237 and a ground lead 239 which extend through cable 110 to electronics module 103.

The degree to which permanent magnet 223 extends into electro-magnet 227 depends on the forces applied by the latter and by leaf spring 229. A cyclical electric signal through coil 235 causes permanent magnet 223 to oscillate relative to the rest of probe 101, causing housing 119 to vibrate. These vibrations can be damped by body 99 when attached by tape 105 to the mechanical interface surface 120 of housing 119. This damping action determines the degree to which the frequency of the vibrations differ from the free-space resonant frequency of probe 101.

Figure 3:
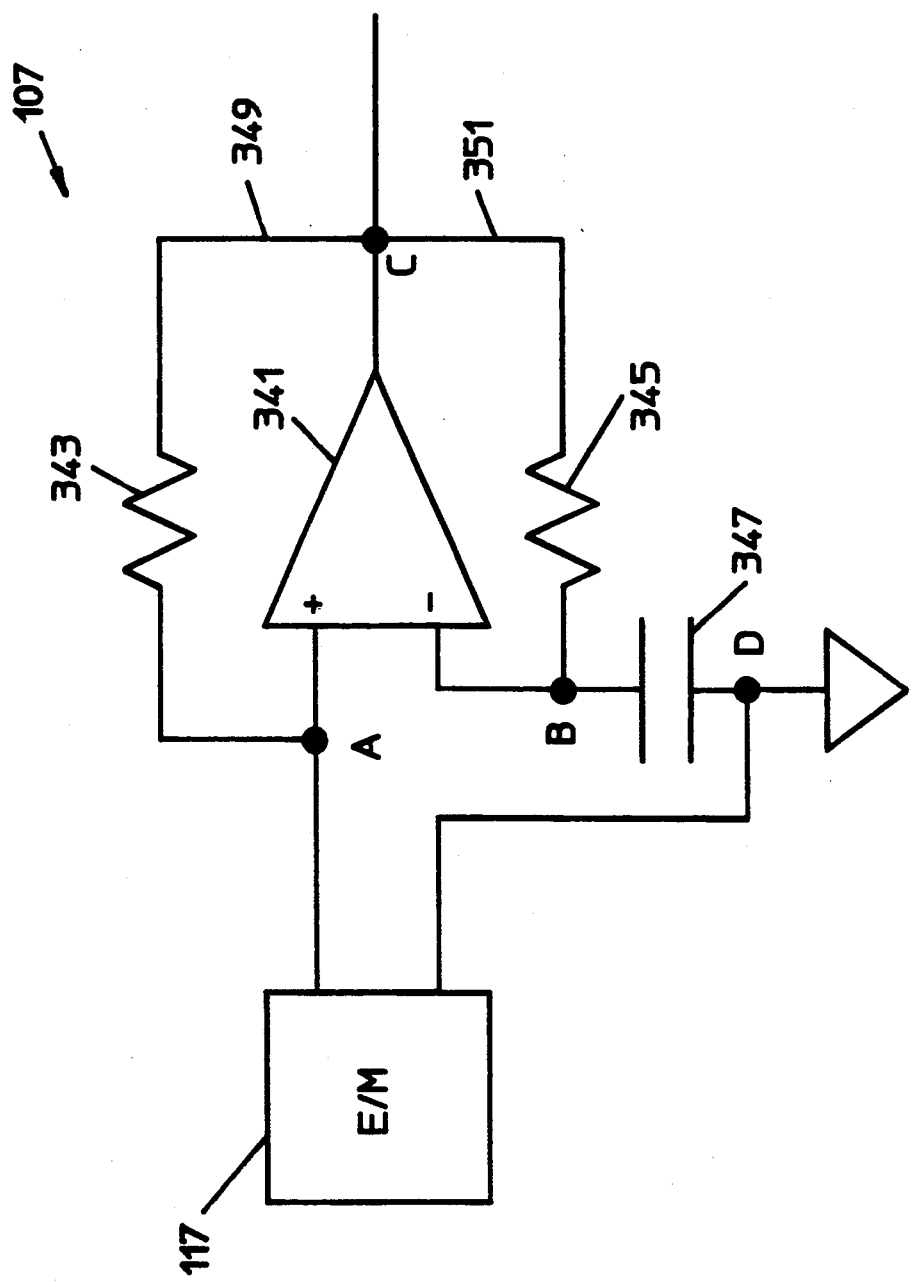
FIG. 3 is a circuit diagram of a drive circuit of the system of FIG. 1 shown in relation to the probe of FIGS. 2A and 2B.

Drive circuit 107 is designed to drive probe 101 at its resonant frequency, as modified by the mechanical impedance of body 99 when attached. Drive circuit 107 comprises a differential amplifier 341, a positive feedback resistor 343, a negative feedback resistor 345 and an AC-coupling capacitor 347, as shown in FIG. 3. Lead 237 from coil 235 of probe 101 is coupled to node A of drive circuit 107, while lead 239 is coupled to node D, which is at ground. Node A is coupled to the "+" input of differential amplifier 341. The "−" input of differential amplifier 341 is AC-coupled to ground via capacitor 347.

The output of differential amplifier 341 at node C is fed back to node A and thus to "+" terminal of amplifier 341 via a positive feedback loop 349 including resistor 343. The output at node C is also fed back to node B and thence to the "−" input of amplifier 341 via a negative feedback loop 351 including resistor 345. In the illustrated embodiment, positive feedback resistor 343 is nominally 100 k$\Omega$, negative feedback resistor 345 is nominally 500 k$\Omega$, and capacitor 347 is nominally 10 $\mu$F. By contrast, the DC resistance of the transducer is of the order of 5 $\Omega$. At the resonant frequency of the transducer, the voltage swings at the "+" terminal of amplifier 341 due to the positive feedback signal are larger than the voltage swings at the "−" terminal of amplifier 341 due to the negative feedback signal. Thus, although the amplifier is stably biased, the system oscillates at the resonant frequency.

The amplifier output not only drives probe 101 according to the signal at node A, but also provides via node C a buffered signal at node E, shown in FIG. 1, of output section 109 for driving frequency display 111 and frequency-to-voltage converter 113 for driving strip-chart recorder 115.

Figure 4:
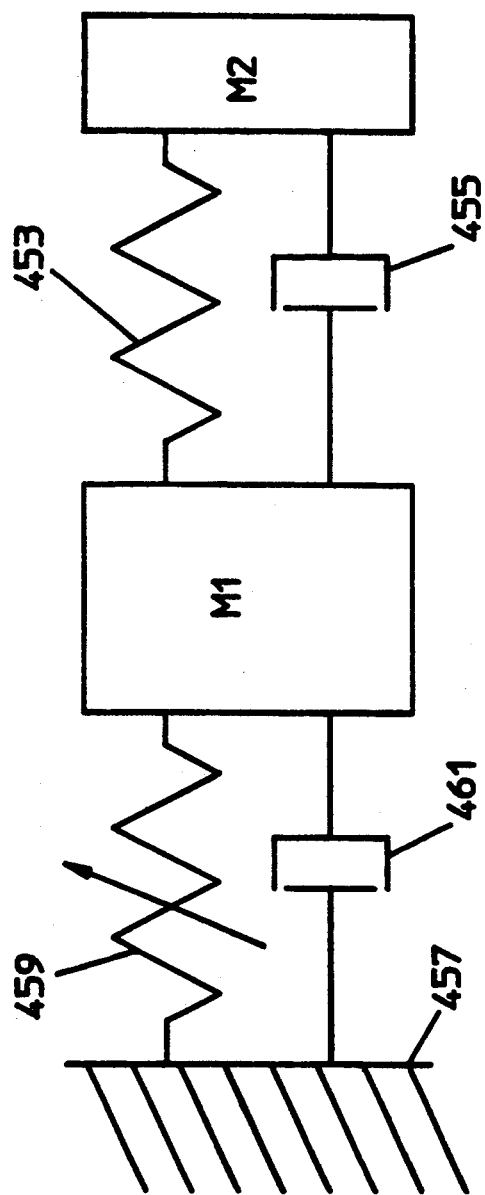
FIG. 4 is a schematic diagram of a mechanical model of the probe of FIGS. 2A and 2B.

The action of probe 101 can be further understood with reference the mechanical model of FIG. 4. Probe 101 can be represented by a mass $M_1$, corresponding collectively to housing 119, cap 121 and electro-magnet 225, a mass $M_2$ corresponding to permanent magnet 223, and a spring force 453, corresponding to leaf spring 229. In addition, mechanical resistance of probe 101 is represented by dashpot 455. Body 99 is modelled by an infinite rigid mass 457, variable spring 459 and dashpot 461. (In a more complete model, $M_1$ would include a component representing bodily tissue displaced by the action of probe 101.) The spring constant of variable spring 459 varies with changes in mechanical impedance of body 99 which occur during contractions.

When not attached to body 99, probe 101 has a free-space resonant frequency of:

$$f_{fs}=[K(M_1+M_2)/(M_1M_2)]^{\frac{1}{2}}.$$

If attached to a rigid body of infinite mass, probe 101 would have a resonant frequency of:

$$f_\infty=(K/M_2)^{\frac{1}{2}}.$$

The preferred range of oscillation frequencies is from about 20 Hz to 80 Hz. $F_{fs}$ for the illustrated embodiment is about 50 Hz. In the cases of interest, the resonant frequency is intermediate between $f_{fs}$ and $f_\infty$ and varies with the mechanical impedance of body 99.

Figure 5:
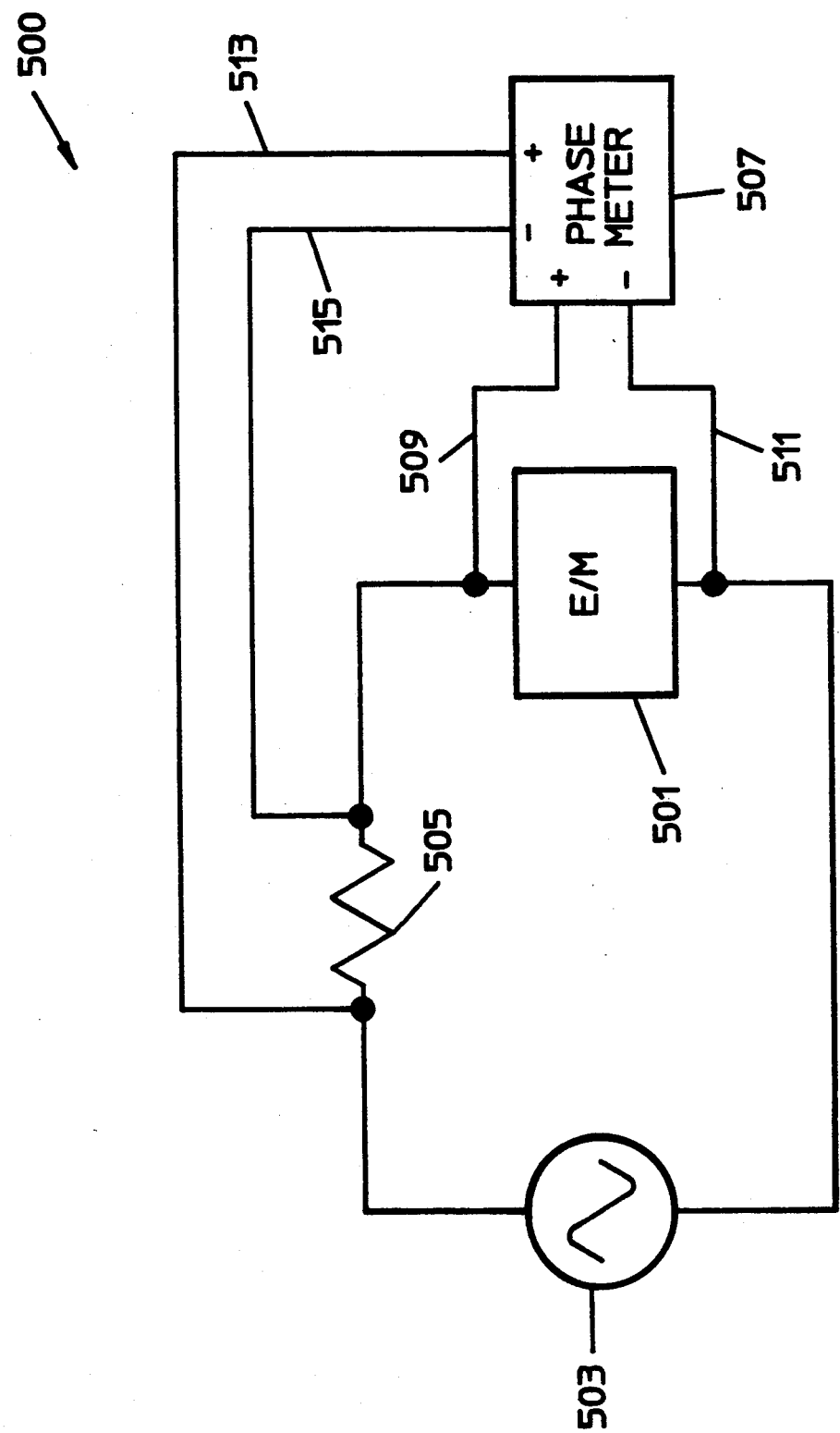
FIG. 5 is a block diagram of an alternative uterine contraction tracing system in accordance with the present invention.

In uterine contraction tracing system 100 described above, changes in resonant frequency are detected by driving transducer 117 at resonant frequency and monitoring the drive frequency. In an alternative uterine contraction tracing system 500, shown in FIG. 5, a drive signal is maintained at a constant frequency and changes in resonant frequency are detected by monitoring the phase relationship between the current and the voltage across a transducer 501.

System 500 comprises transducer 501, an AC voltage source 503, a resistor 505 and a phase meter 507. Transducer 501 and resistor 505 constitute a transducer assembly. Voltage source 503 drives transducer 501 at a constant frequency. Phase meter 507 detects the voltage across transducer 501 via lines 509 and 511 and the voltage across resistor 505 via lines 513 and 515 and measures the phase differential between the two voltages. The voltage across resistor 505 is in phase with the current through transducer 501 so that the phase differential measured by phase meter 507 is the difference between the phases of the voltage and current through transducer 501.

When transducer 501 is interfaced with a body and the mechanical impedance of that body changes, the resonant frequency of transducer 501 changes. Because AC voltage source 503 drives transducer 501 at a constant frequency, the difference between the drive frequency and the resonant frequency changes with resonant frequency. This frequency difference results in a phase difference measured by phase meter 507. Thus, phase meter 507 can be used to indicate changes in mechanical impedance, for example, such as those caused by uterine contractions.

An alternative embodiment employs a transducer with two electromagnets, rather than one electromagnet and one permanent magnet. Another embodiment uses a transducer fabricated by modifying an small, inexpensive loudspeaker by cutting away portion of the cone and adding mass to lower its resonant frequency to about 50 Hz. Also, when a body is appropriately positioned, the incorporated probe can be held in position by gravity so that tape is not required.

In the illustrated embodiment, contractions are detected because changes in mechanical impedance of the contracting tissues affect the frequency output from a resonant circuit. However, the present invention provides for non-resonant circuit. However, the present invention provides for non-resonant circuits as well. In an alternative embodiment, a motor drives an eccentric shaft, e.g., a shaft with an off-center weight attached. A constant current drives the motor at a constant rotational rate. The eccentric shaft causes an attached frame to vibrate. The motor thus serves as a non-resonant electro-mechanical transducer. When the frame is pressed against a body, the rotation rate of the motor varies with changes in the mechanical impedance of the body during contractions. Thus, one can monitor contractions by observing changes in the motor rotation rate.

The foregoing discussion has focussed on frequency as the parameter of interest in detecting contractions. However, other parameters can be used. For example, changes in mechanical impedance can affect the amplitude of a current through an electro-magnetic resonator.

While contractions can be detected by examining the effect of changes in mechanical impedance on an electro-mechanical transducer, it is also possible to characterize contractions by their effect on the signal generated from such a transducer. During a contraction, there is a change in the effect of bodily tissue on signal amplitude and phase. These changes can be detected as the signal is received after being transmitted through or reflected by the body. One embodiment uses pseudo-random numbers to generate a signal. An advantage of this pseudorandom approach is that the resulting signal is broad spectrum and thus minimally disturbing to a subject. In addition, such signals are easily distinguished from noise, even where the latter's amplitude is relatively high. Alternatively, the generated signal can be pulses generated by a series of taps. The changing delays in the transmitted or reflected signal can be used to characterize a contraction.

In related embodiments, the tendency of a change in mechanical impedance to change frequency can be compensated by changing another variable, e.g., drive current. In this case, contractions are not reflected in frequency changes since frequency is held constant. However, contractions can be traced by tracking the drive current required to maintain constant amplitude or, in the eccentric shaft embodiment, rotation rate.

While tracing system 100 detects changes in mechanical impedance by monitoring the drive signal, the present invention provides alternatives. For example, a separate acoustic receiver can be used to detect acoustic waves transmitted through or reflected by a body.

A uterine contraction system can incorporate multiple probes for current detection of changes in mechanical impedance at several locations on a body. Multiple probes cannot be used conveniently with the current method, because multiple belts would be required. The present invention provides for a multiple probe system which can be used to monitor the progress of single contractions. This monitoring can be used to distinguish contractions from localized false labor contractions which could confuse a single probe system. In addition, while a single probe system might fail to detect contractions due to probe misplacement, a multiple probe system would be much less susceptible to this problem.

The present application is described above as applied to the detection of uterine contractions. More generically, the principles involved in the present invention include the modulation of signals by changes in mechanical impedance of a body. With appropriate modifications, the system and method of the present invention can be used to detect changes in mechanical impedance in tissue reflecting other physiological events, such as voluntary muscular activities. Furthermore, applications of the present invention are not limited to physiological phenomena, but can include measurement of tension, rigidity and viscosity where desired. These and other modifications and variations are provided for by the present invention, the scope of which is limited only by the following claims.

What is claimed is:

1. A system for detecting contractions in and adapted for coupling to a human body, said body having a variable mechanical impedance which changes with contractions, said system comprising:
   a transducer including a relatively rigid interface having a first side for contacting the body and a second side disposed away from the body;
   vibrating means being arranged for converting drive signals into vibrations and being connected to said second side of the transducer so that vibrations can be mechanically coupled by said relatively rigid interface into said body, said vibrations having a frequency which varies with the mechanical impedance of said body;
   a drive circuit coupled to said vibrating means for providing a drive signal thereto; and
   monitor means coupled to said drive circuit and said vibration means for detecting contractions.

2. The system of claim 1 wherein said transducer has a resonant frequency which changes with changes in the mechanical impedance of said body, said drive circuit incorporating feedback so that it drives said transducer at its resonant frequency, said monitor means monitoring said resonant frequency to detect changes in the mechanical impedance of said body.

3. The apparatus as in claim 1, wherein said monitor means detects contractions as changes in said vibration frequency.

4. The apparatus as in claim 1, wherein:
   said drive circuit changes said drive signal for keeping said vibration frequency constant, and
   said monitor means responds to changes in said drive signal to detect contractions.

5. The apparatus as in claim 4 wherein the drive signal is an electrical signal.

6. The apparatus as in claim 1 wherein the vibrating means includes a motor for driving an eccentric shaft to produce the vibrations.

7. The apparatus of claim 1, wherein:
   said drive circuit produces an electrical current signal having a variable amplitude; and
   said monitor means operates to measure changes in amplitude of the electrical signal.

* * * * *